(12) United States Patent
Ryan et al.

(10) Patent No.: US 8,460,248 B2
(45) Date of Patent: *Jun. 11, 2013

(54) ENDOSCOPIC BITE GUARD AND RELATED METHODS OF USE

(75) Inventors: Shawn Ryan, Upton, MA (US); Robert B. DeVries, Northborough, MA (US); Christopher A. Benning, Lowell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 573 days.

This patent is subject to a terminal disclaimer.

(21) Appl. No.: 12/639,426

(22) Filed: Dec. 16, 2009

(65) Prior Publication Data

US 2010/0154791 A1 Jun. 24, 2010

Related U.S. Application Data (60) Provisional application No. 61/193,723, filed on Dec. 18, 2008.

(51) Int. Cl.
*A61M 5/32* (2006.01)
(52) U.S. Cl.
USPC .................. 604/174; 128/200.24; 128/200.26
(58) Field of Classification Search
USPC ........... 604/174; 128/200.26, 200.24, 207.14, 128/207.15
See application file for complete search history.

(56) References Cited

U.S. PATENT DOCUMENTS

| 6,029,668 | A | 2/2000 | Freed |
| 7,160,270 | B2 * | 1/2007 | West et al. ..................... 604/174 |
| 2002/0095118 | A1 | 7/2002 | Bertoch et al. |
| 2002/0162555 | A1 | 11/2002 | West et al. |

FOREIGN PATENT DOCUMENTS

| WO | WO 96/11029 A1 | 4/1996 |
| WO | WO 9611029 A1 * | 4/1996 |

OTHER PUBLICATIONS

International Search Report and Written Opinion issued in PCT International Application No. PCT/US2009/068397 mailed Apr. 23, 2010 (16 pages).

* cited by examiner

*Primary Examiner* — Laura A Bouchelle
(74) *Attorney, Agent, or Firm* — Bookoff McAndrews, PLLC (57) ABSTRACT

A medical device may include a bite guard assembly configured to restrict sliding movement of an elongated member relative to the bite guard assembly. The bite guard assembly may include a main portion including a mouthpiece. The main portion may include a surface defining a passageway for receipt of the elongated member therethrough. The bite guard assembly may also include a securing portion configured to restrict movement of the elongated member through the passageway and that is configured to be disposed between the surface and the elongated member.

20 Claims, 4 Drawing Sheets

ENDOSCOPIC BITE GUARD AND RELATED METHODS OF USE

DESCRIPTION OF THE INVENTION

This application claims the benefit of priority from U.S. Provisional Application No. 61/193,723, filed Dec. 18, 2008, which is herein incorporated by reference in its entirety.

FIELD OF THE INVENTION

Embodiments of the present invention relate to endoscopic bite guards. In particular, exemplary embodiments of the present invention relate to endoscopic bite guards for use with a guide tube. Embodiments of the present invention also cover methods of using such devices.

BACKGROUND OF THE INVENTION

In general, it is desirable to minimize the invasiveness of medical procedures. These medical procedures may include therapeutic or diagnostic medical procedures. Invasive medical procedures are generally more expensive, and there is generally a greater risk of complication and discomfort for the patient. For example, open surgery, for a therapeutic or diagnostic purpose, is an invasive medical procedure with significant attendant risks. Since the performance of open surgery typically requires relatively large incisions, relatively large amounts of blood may be lost, the risk of infection may increase, and the potential for post-operative hernias may be higher. Furthermore, relatively large incisions require extended recovery times to allow the incisions to heal.

Laparoscopic procedures are generally less invasive than open surgery. Percutaneous endoscopic gastrostomy (PEG) is a laparoscopic procedure that involves incisions through the skin to access various body organs. For example, PEG may provide access through the skin to the stomach to allow insertion of a feeding tube for feeding patients who cannot ingest food on their own. The incisions, however, may lead to a risk of infection and other negative effects, such as sepsis, which can be caused by leakage of septic fluid contained in the stomach.

Another type of surgical procedure is a transluminal endoscopic surgical procedure, which may allow access to various body organs without having to puncture the skin, which may lead to infection due to exposure to the outside environment. In transluminal endoscopic surgical procedures, an endoscope may be introduced into the body, for example, through a body orifice (e.g., the rectum or mouth). The endoscope is a flexible instrument introduced into the body to access the inside of the body. A light source and a camera may be provided at a distal end (i.e., the end which is inside the body) of the endoscope to direct an image from inside the body to a monitor, or other similar viewing device, positioned outside the body. An endoscopist may use this image to position the distal end of the endoscope at a desired location within the body. Once the endoscope is positioned at a desired work site within the body, the endoscopist may perform any desired therapeutic or diagnostic procedure at the work site.

Exemplary diagnostic procedures that may be performed using an endoscope include, among others, endoscopic ultrasound-guided fine needle aspiration (EUS-FNA) and endoscopic retrograde cholangiopancreatography (ERCP). EUS-FNA is a diagnostic procedure used to obtain biopsy samples from suspected malignant lymph nodes within the body. In an exemplary EUS-FNA procedure, a distal end of the endoscope is positioned proximate a malignant-appearing lymph node, and the node excited with ultrasound vibrations delivered through the endoscope. Fine needle aspiration is then performed by inserting a needle into the lymph node to collect cytological material therefrom. ERCP is used to diagnose and treat conditions of the bile ducts, such as, gallstones, inflammatory strictures, etc. An endoscope is inserted into the stomach and the distal end positioned proximate the bile duct. Dyes may then be injected into the bile duct so that they may visible on x rays.

In some procedures, the endoscopic instrument may be used to puncture a wall of the stomach or other organ to allow the distal end of the endoscope to advance into the abdominal cavity or other organ where remotely controlled surgical or diagnostic tools may be used to perform desired surgical or diagnostic procedures. In general, for endoscopic procedures, it may be difficult to position the endoscope within a cavity of the body while at the same time being able to manipulate the surgical tools or diagnostic to perform the desired procedures.

It is to be understood that both the foregoing general description and the following detailed description are exemplary and explanatory only and are not restrictive of the invention, as claimed.

SUMMARY OF THE INVENTION

An embodiment of the invention may include a medical device. The medical device may include a bite guard assembly configured to restrict sliding movement of an elongated member relative to the bite guard assembly. The bite guard assembly may include a main portion including a mouthpiece. The main portion may include a surface defining a passageway for receipt of the elongated member therethrough. The bite guard assembly may also include a securing portion configured to restrict movement of the elongated member through the passageway. The securing portion may be configured to be disposed between the surface and the elongated member.

Various embodiments of the invention may include one or more of the following aspects: the securing portion may be configured to form a friction or interference fit with the elongated member; the securing portion may include a projection configured to be inserted between the elongated member and the surface of the bite guard assembly; the projection may include a wedge member; the wedge member may be configured to interface with the surface and the elongated member and restrict movement of the elongated member through the passageway; the wedge member may include one or more protrusions that extend from the wedge member, the one or more protrusions may be configured to interface with the elongated member and restrict movement of the elongated member through the passageway; the elongated member may include one or more protrusions configured to interface with the wedge member and restrict movement of the elongated member through the passageway; the bite guard assembly may further include a connecting member connecting the projection to the main portion of the bite guard assembly; the bite guard assembly may be configured to include a gap between the elongated member and the surface to allow air to pass therethrough; the projection may be configured to form a friction or interference fit with the elongated member; the securing portion may include a plurality of projections on the surface and extending toward a center of the passageway.

Various embodiments of the invention may also include one or more of the following aspects: the projections may be configured to form a friction fit with the elongated member; the bite guard assembly may further include an expandable member on the surface, the expandable member may include a channel, and the securing portion may include a projection configured to be inserted into the channel in the expandable member; the expandable member may be configured to transform from a collapsed configuration to an expanded configuration when the projection is inserted into the channel; the expanded configuration may be a configuration where the expandable member interfaces with the elongated member to restrict movement of the elongated member relative to the bite guard assembly; the bite guard assembly may further include a connecting member connecting the projection to the main portion of the bite guard assembly; the projection may be conical; the expandable member may be configured to form a friction or interference fit with the elongated member when the projection is inserted into the channel in the expandable member; the elongated member may be a flexible guide tube; the main portion and the securing portion may be configured to restrict movement of elongated members of varying diameters.

Another embodiment of the invention may include a method of inserting a guide tube into a patient. The method may include advancing a guide tube through a passageway in a main portion of a bite guard assembly. The bite guard assembly may be capable of restricting the movement of the guide tube, and advancing the guide tube into a body lumen.

Various embodiments of the invention may include one or more of the following aspects: the bite guard assembly may include a securing portion restricting the movement of the guide tube through the passageway, the securing portion may be configured to be disposed between the guide tube and a surface defining the passageway; the method may further include forming a friction or interference fit with the securing portion and the guide tube; the method may further include inserting a projection of the securing portion between the guide tube and the surface; the projection may include a wedge member; the wedge member may include one or more protrusions that extend from the wedge member, the one or more protrusions may be configured to interface with the guide tube and restrict movement of the guide tube through the passageway; the guide tube may include one or more protrusions configured to interface with the wedge member and restrict movement of the guide tube through the passageway; the bite guard assembly may include a connecting member that connects the projection to the main portion of the bite guard assembly; the method may further include allowing air to pass through the passageway in the bite guard assembly when the guide tube is in the passageway;

Various embodiments of the invention may also include one or more of the following aspects: the method may further include forming a friction or interference fit with the projection and the guide tube; the method may further include forming a friction fit with the guide tube and a plurality of protrusions disposed on the surface, the securing portion may include the protrusions, and the protrusions may extend toward a center of the passageway; the method may further include inserting a projection of the securing portion into a channel in an expandable member in the bite guard assembly, the expandable member may be disposed on the surface; inserting the projection into the channel may include changing the expandable member from a collapsed configuration to an expanded configuration, the expandable member may be in the collapsed configuration when the projection is not in the channel; the expandable member may interface with the guide tube to restrict the movement of the guide tube through the passageway when the expandable member is changed to the expanded configuration.

Various embodiments of the invention may also include one or more of the following aspects: the bite guard assembly may include a connecting member that connects the projection to the main portion of the bite guard assembly; the projection may be conical; the method may further include forming a friction or interference fit with the expandable member and the guide tube when the projection is inserted into the channel in the expandable member; the body lumen may include one of a gastrointestinal tract, a pulmonary tract, and an anal tract; the method may further include using one hand to advance the guide tube through the passageway, and using the one hand to advance the guide tube into the body lumen, the method may also include using a second hand to control at least one instrument inserted into a lumen in the guide tube; the method may further include using the second hand to release the at least one instrument, and using the second hand to set the bite guard assembly to restrict the movement of the guide tube; the method may further include using the one hand to release the guide tube, and using the one hand and the second hand to control the at least one instrument after setting the bite guard assembly to restrict the movement of the guide tube; the using of the second hand to set the bite guard assembly to restrict the movement of the guide tube may include using the second hand to insert a projection between the guide tube and a surface defining the passageway of the bite guard assembly while holding the guide tube with the one hand; the projection may include a wedge member.

Various embodiments of the invention may further include one or more of the following aspects: the method may further include allowing air to pass through the passageway in the bite guard assembly when the guide tube is in the passageway; using the second hand to set the bite guard assembly to restrict the movement of the guide tube may include using the second hand to insert a projection into a channel in an expandable member in the bite guard assembly, the expandable member may be disposed on a surface defining the passageway; the method may further include changing the expandable member between an expanded configuration when the projection is inserted into the channel in the expandable member and a collapsed configuration when the projection is not inserted into the channel; the projection may be conical; the method may further include forming a friction fit with the guide tube and a plurality of projections disposed on a surface defining the passageway, the projections may extend toward a center of the passageway; the method may further include using the one hand to release the guide tube, and using the one hand and the second hand to control the at least one instrument; the method may further include selecting the bite guard assembly that corresponds to the guide tube; selection of the bite guard assembly may be based on a dimension of the guide tube.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to exemplary embodiments of the invention, examples of which are illustrated in the accompanying drawings. Wherever possible, the same reference numbers will be used throughout the drawings to refer to the same or like parts.

Figure 1:
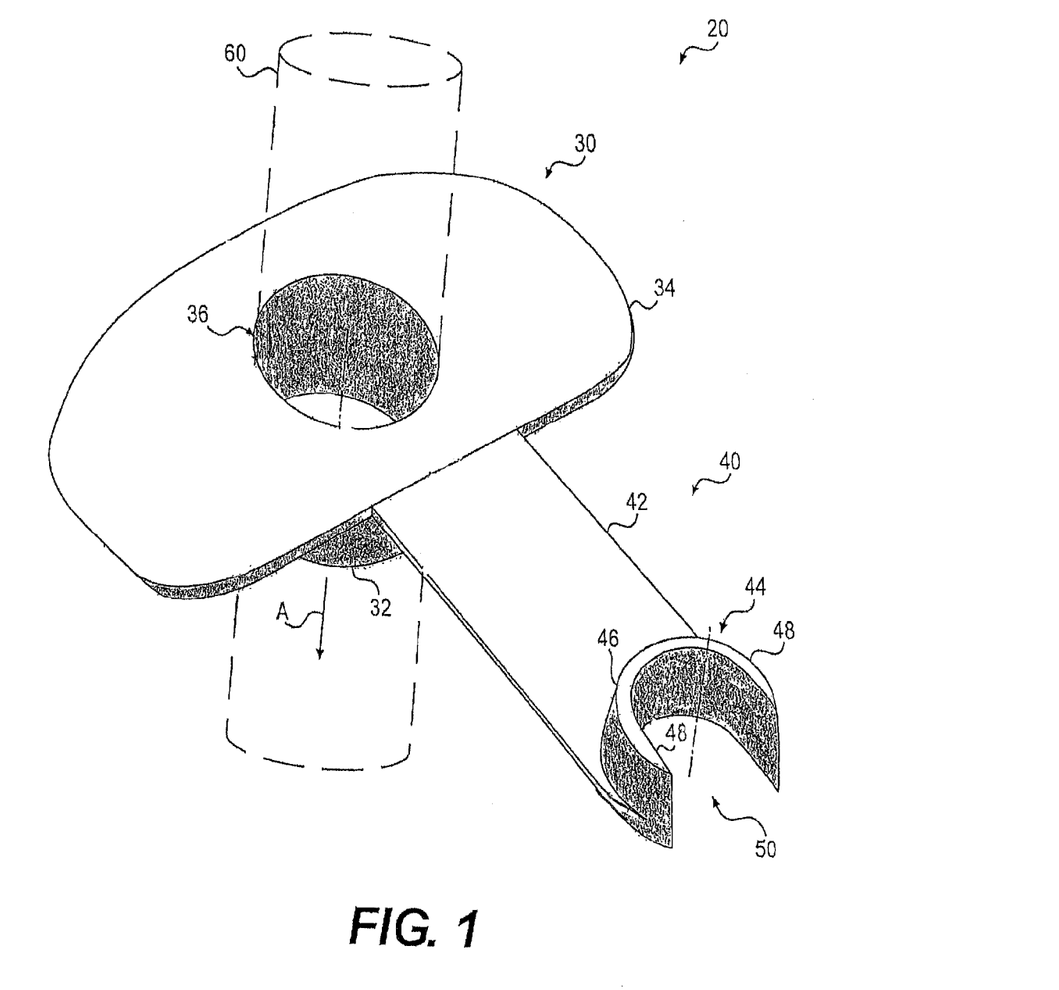
FIG. 1 is a perspective view of a bite guard assembly with a disengaged securing portion, according to an exemplary embodiment of the invention.
Figure 2:
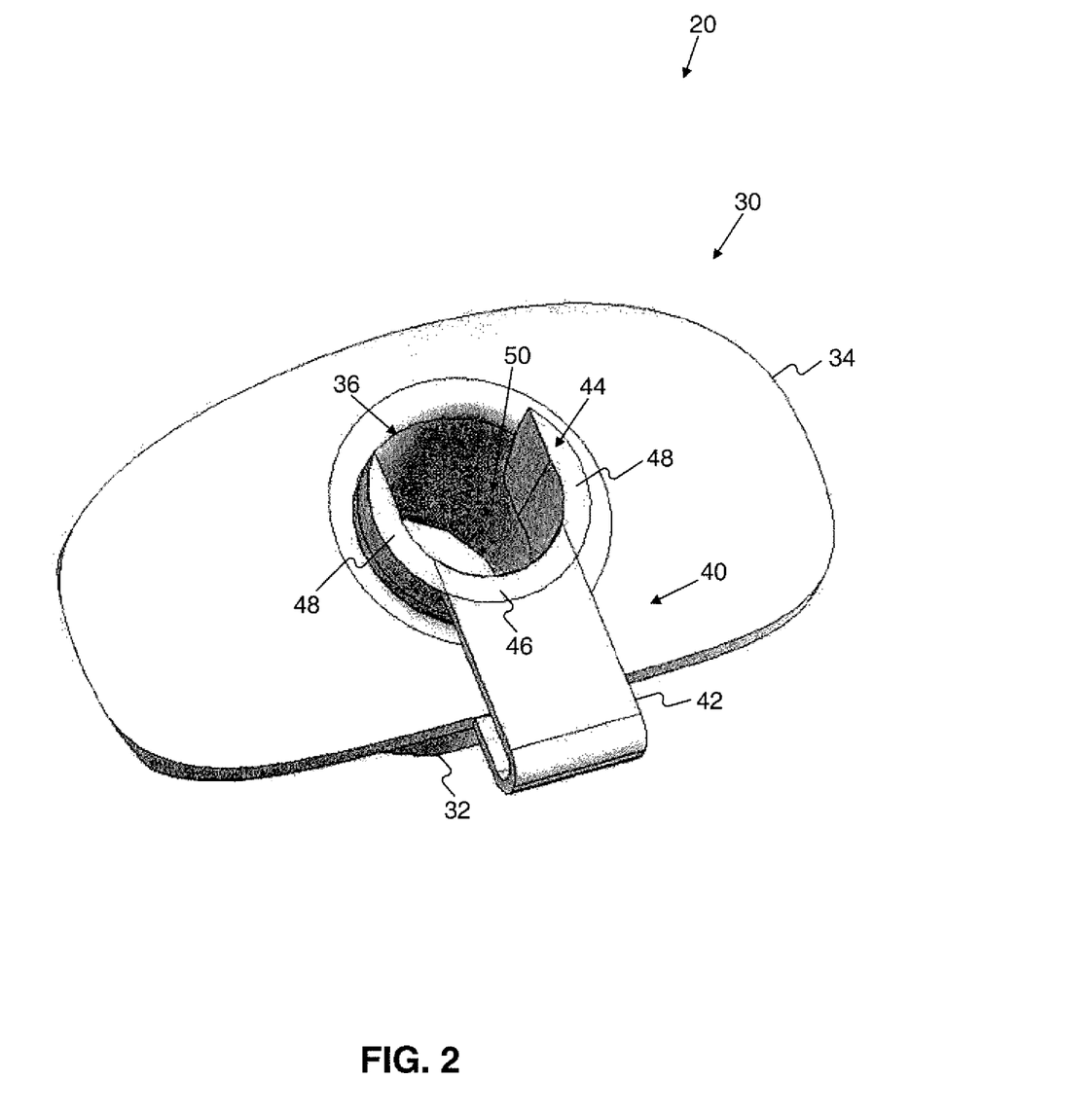
FIG. 2 is a perspective view of the exemplary bite guard assembly of FIG. 1 with an engaged securing portion.

FIGS. 1 and 2 depict an exemplary bite guard assembly 20 that may be used for any therapeutic or diagnostic endoscopic procedure. In this disclosure, endoscopic procedure is broadly used to indicate any medical procedure that may be performed by inserting an endoscope, guide tube, catheter, or any other medical device into the body through any anatomic opening. Although in the description that follows, an endoscopic procedure, wherein a endoscope is inserted into the body through the mouth is described, it should be emphasized that this description is exemplary only. In general, embodiments of the current disclosure may be applicable to any application where a medical device is inserted into the body through an anatomic opening.

Bite guard assembly 20 may be positioned on and secured to a guide tube (not shown), such as an endoscope. The guide tube may be configured to be advanced through any body lumen. These body lumens may include, among others, the gastrointestinal tract (GI tract), the pulmonary tract, and the anal tract. The G1 tract may include the mouth, the esophagus, the stomach, and all associated body cavities; the pulmonary tract may include the ear, the nose, the throat and all associated body cavities; and the anal tract may include the anal cavity, the rectum, the colon and all associated body cavities. The guide tube may have a distal end and a proximal end, and may be made of any suitable material, e.g., a suitable biocompatible material, capable of being advanced through a body lumen. The guide tube may include an elongated member 60 extending between the distal end and a proximal end. The elongated member 60 may be flexible, for example, to be able to traverse tortuous anatomy. The distal end may include the end of the guide tube internal to the body and the proximal end may include the end of the guide tube external to the body.

According to an embodiment, the guide tube may be inserted through the mouth. The guide tube may be advanced through the esophagus and then inserted into the stomach of the patient. As an example, the guide tube may include a device for making an incision through a wall of the stomach or other body tissue, such as a wall of another body organ. The guide tube may then pass through the incision to operate at a work site. The work site could include, for instance, a part of the small intestine, another organ within the abdominal cavity, or other body organ. Alternatively, as indicated earlier, embodiments of the current disclosure may be applied to any endoscopic application known in the art.

A lumen may run longitudinally through the elongated member of the guide tube and may include a hollow cavity configured to deliver an endoscopic instrument to the work site. The lumen may extend between the distal end and the proximal end of the guide tube. Alternatively, one or more additional lumens, e.g., one or more of an aspiration lumen, an irrigation lumen, an illumination lumen, a viewing lumen, and a working lumen, may run longitudinally through the elongated member.

As shown in FIGS. 1 and 2, the bite guard assembly 20 can be configured to allow the patient to bite down on the bite guard assembly 20 to allow the patient to grip the bite guard assembly 20 between opposed teeth of the upper and lower jaws in the patient's mouth. The bite guard assembly 20 may be made of any suitable material, e.g., a suitable biocompatible material capable of being bitten and secured between the patient's jaws, such as rubber or plastic.

The distal end of the guide tube may be inserted in the patient's mouth and advanced through the esophagus and into the stomach. The bite guard assembly 20 may be disposed about the guide tube on or near the proximal end and may be configured to allow the elongated member to move freely, or to restrict the movement of the elongated member.

Bite guard assembly 20 may include a main portion 30 and a securing portion 40. The main portion 30 may include a tubular mouthpiece 32 and a front shield 34. The mouthpiece 32 may be formed integrally with the shield 34. A passageway 36 may be formed by an inner surface of the mouthpiece 32 and the shield 34, and the elongated member may be slidably disposed in the passageway 36. The passageway 36 may be cylindrical or have another shape that allows the guide tube to pass through the passageway 36.

The shield 34 may include a pair of strap openings (not shown). One or more straps may be attached to the strap openings. For example, a pair of straps connected to the strap openings may wrap around the back of the patient's head to secure the bite guard assembly 20 in place. The straps may be provided with a fastening mechanism that may be adjustable to vary the fit of the straps around the patient's head. For example, the fastening mechanism may include a plurality of locking nubs on one strap and a plurality of holes on the other strap.

The securing portion 40 may include a connecting member 42 and a projection, such as wedge member 44. The connecting member 42 may be a strap or another type of connector. The connector may include a hinge, such as a living hinge (e.g., a piece of material including a thin section that bends to allow movement and that is made using an injection molding process). The connecting member 42 may be formed from a flexible material, such as a plastic, rubber, malleable metal or fabric material, to allow the wedge member 44 to be inserted into the passageway 36 in the main portion 30 of the bite guard assembly 20. Alternatively, the connecting member 42 may be omitted such that the wedge member 44 is not connected to the main portion 30 of the bite guard assembly 20.

The wedge member 44 may be configured to be inserted into the passageway 36 in the main portion 30 of the bite guard assembly 20 when the elongated member of the guide tube is also disposed in the passageway 36. According to the embodiment shown in FIGS. 1 and 2, the wedge member 44 may be inserted into a gap between the elongated member of the guide tube and the passageway 36. The wedge member 44 may be formed from a material, e.g., plastic or rubber, that is capable of forming a friction or interference fit with the elongated member of the guide tube. As a result, the wedge member 44 may secure the bite guard assembly 20 onto the guide tube through friction or interference. Insertion of the wedge member 44 may help to prevent inadvertent movement of the elongated member with respect to the bite guard assembly 20.

FIG. 1 shows the wedge member 44 removed from the passageway 36 such that the wedge member 44 is disengaged, and FIG. 2 shows the wedge member 44 inserted into the passageway 36 such that the wedge member 44 is engaged. After engaging the wedge member 44 by inserting it between the elongated member of the guide tube and the passageway 36, the wedge member 44 may be removed or disengaged to allow an adjustment of the location of the bite guard assembly 20 on the guide tube, and positioning of the guide tube in the body.

The wedge member 44 may be sized to be compatible with guide tubes of different sizes. Furthermore, wedge member 44 may be sized or shaped to allow a portion of the gap between the elongated member of the guide tube and the passageway 36 to remain unobstructed, thereby allowing air to flow freely into and out of the patient's mouth. Wedge member 44 may include breathing holes and lumens running through the wedge to allow airflow or fluid flow. Optionally, the wedge member 44 may include a tab (not shown) or other feature for allowing the operator to remove the wedge member 44 from between the elongated member of the guide tube and the passageway 36. Attachment of wedge member 44 to the main portion 30 of the bite guard assembly 20 is mainly for convenience. In general, wedge member 44 may include a separate part. In some embodiments, wedge member 44 may also include multiple parts that cooperate together to retain guide tube in passageway 36.

According to one embodiment, as shown in FIGS. 1 and 2, the wedge member 44 may be approximately U-shaped and may include a curved portion 46 with arms 48. The curved portion 46 of the wedge member 44 may have a diameter that is greater than the diameter of the elongated member of the guide tube and less than the diameter of the passageway 36. Accordingly, a gap 50 between the arms 48 of the wedge member 44 allows the wedge member 44 to slide onto the guide tube such that the curved portion 46 and the arms 48 may be inserted between the elongated member of the guide tube and the passageway 36.

The operator may select the bite guard assembly 20 from a set of similar bite guard assemblies of various sizes. For example, the size of the bite guard assembly 20 (e.g., dimensions of the mouthpiece 32, the shield 34, and/or the wedge member 44) may vary according to the patient's anatomy (e.g., the size of the patient's mouth, the distance between the mouth and nose, or other dimension), the size (e.g., diameter or other dimension) of the elongated member of the guide tube to be inserted into the passageway 36, etc. In addition, other characteristics of the bite guard assembly 20 may vary. After selecting the appropriate bite guard assembly 20, the selected bite guard assembly 20 may be inserted into the patient's mouth to allow the patient to grip the mouthpiece 32 of the bite guard assembly 20.

According to one embodiment, the guide tube may be used to deliver working instruments (e.g., an endoscope or other instruments including the device for taking biopsy samples, making an incision, a camera, etc.) to the work site. The working instruments may be delivered to the work site through the lumen of the guide tube so that the working instruments may be used to operate inside the body, e.g., to create an incision in the stomach wall or other body tissue. The guide tube may also be used as a reference frame so that the adjustment of the guide tube with respect to the bite guard assembly 20, e.g., by moving in the direction of arrow A or in the opposite direction, allows the lengthening or shortening, respectively, of the amount of the guide tube in the body. As a result, the position of the working instruments within the body may depend on the position of the bite guard assembly 20 on the guide tube and the position of the guide tube in the body.

For example, the guide tube may be inserted into the bite guard assembly 20 in the direction of arrow A and then into the patient's GI tract until the distal end of the guide tube is positioned, e.g., at a floor of the stomach or duodenum. One or more working instruments may be inserted into the lumen in the guide tube. The working instruments may be controlled while the guide tube is advanced into the GI tract.

To hold the guide tube in place with respect to the GI tract and the bite guard assembly 20 (e.g., so that the operator may free both hands to control the working instruments in the guide tube), the operator may engage the wedge member 44 by inserting it between the elongated member of the guide tube and the passageway 36. Optionally, before inserting the wedge member 44, the operator may engage a locking mechanism (not shown) to secure the working instruments in place in the lumen of the guide tube. The position of the elongated member of the guide tube with respect to the bite guard assembly 20 may remain generally constant until the wedge member 44 is removed. In one embodiment, the working instruments may be manipulated through the guide tube to operate on the gall bladder (e.g., during a cholecystectomy) or other body organ. The guide tube may be used as a frame of reference when inserting the working instruments into the body.

To adjust the position of the guide tube with respect to the GI tract and the bite guard assembly 20, the operator may release the bite guard assembly 20 from the elongated member of the guide tube by disengaging or removing the wedge member 44 from between the elongated member of the guide tube and the passageway 36. The guide tube may be advanced further into the GI tract by continuing to move through the passageway 36 of the bite guard assembly 20, or the guide tube may be retracted by pulling the guide tube in the opposite direction.

The position of the elongated member with respect to the bite guard assembly 20 is adjustable, thereby allowing customization based on the dimensions of the individual patient's anatomy (e.g., the distance between the mouth and the stomach). Furthermore, the wedge member 44 secures the bite guard assembly 20 onto the elongated member when the wedge member 44 is inserted between the elongated member of the guide tube and the passageway 36. Accordingly, the elongated member may be prevented from moving with respect to the patient's GI tract, and the operator does not have to continuously hold the elongated member. Inadvertent movement of the elongated member, e.g., during surgery, may be prevented. In addition, the bite guard assembly 20 controls the placement of the patient's tongue and prevents the patient from biting the elongated member of the guide tube, thereby protecting the guide tube and working instruments inserted into the guide tube. In some embodiments, passageway 36 may be keyed to accept at least one wedge member 44. In some such embodiments, a portion of wedge member 44 may be located within the wall of mouthpiece 32 and a portion of wedge member 44 may extend into passageway 36.

In some embodiments, wedge member 44 may be attached to a guide tube that may be inserted into passageway 36 of mouthpiece 32. In some such embodiments, wedge member 44 may include a component (such as, for instance a ring or an open collar) that fits around the guide tube. The outer surface of such a wedge member may interface with passageway 36 and restrict further movement of the guide tube. Any of the wedge member embodiments, whether located on the mouthpiece, the guide tube, or configured as separate parts, may include mechanisms to secure the wedge member 44 to the mouth piece 32. Embodiments of these securement mechanisms may include tabs that may interface with mating features on the mouthpiece, keying and mating grooves, Velcro® and magnets.

The operator may control the working instruments with one hand while advancing the guide tube into the patient's GI tract with the other hand. For example, after the operator inserts the guide tube into the bite guard assembly 20 and as the guide tube advances through the GI tract, the operator's left hand may coordinate the movement of the working instruments while the operator's right hand may control the positioning of the guide tube in the GI tract. To permit the operator to use both hands to control the working instruments (e.g., to perform certain tasks, such as passing the working instruments through the lumen of the guide tube, manipulating the working instruments, etc.), while holding the elongated member of the guide tube with the right hand, the operator may use the left hand to release the working instruments and insert the wedge member 44 between the elongated member of the guide tube and the passageway 36 to hold the guide tube in place. Then, the operator is free to use both hands to control the working instruments.

Alternatively, instead of inserting the guide tube and the bite guard assembly 20 in the patient's mouth, the guide tube and the bite guard assembly 20 (with appropriate modifications) may be inserted into other anatomic openings in the patient's body, such as the anus, vagina, nose, or other orifice. In such cases, some structural modifications, including the size and shape of the components, may be desired to accommodate the local anatomy of the orifice under intubation. In addition, an entry clamp may be used, when appropriate, to secure the bite guard assembly 20 with respect to the orifice.

Alternatively, the bite guard assembly 20 may include any suitable shape, parts, and/or configurations to allow the bite guard assembly 20 to be secured or locked to the elongated member. For example, FIGS. 3 and 4 illustrate alternate embodiments of the bite guard assembly.

Figure 3:
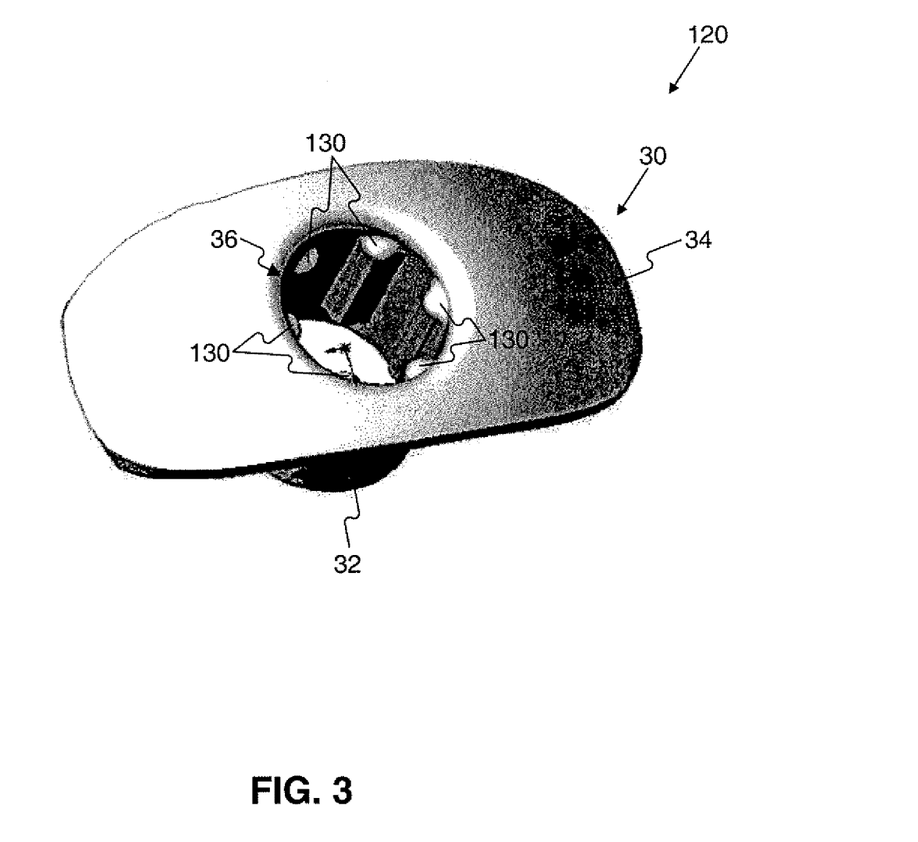
FIG. 3 is a perspective view of a bite guard assembly, according to another exemplary embodiment of the invention.
Figure 4:
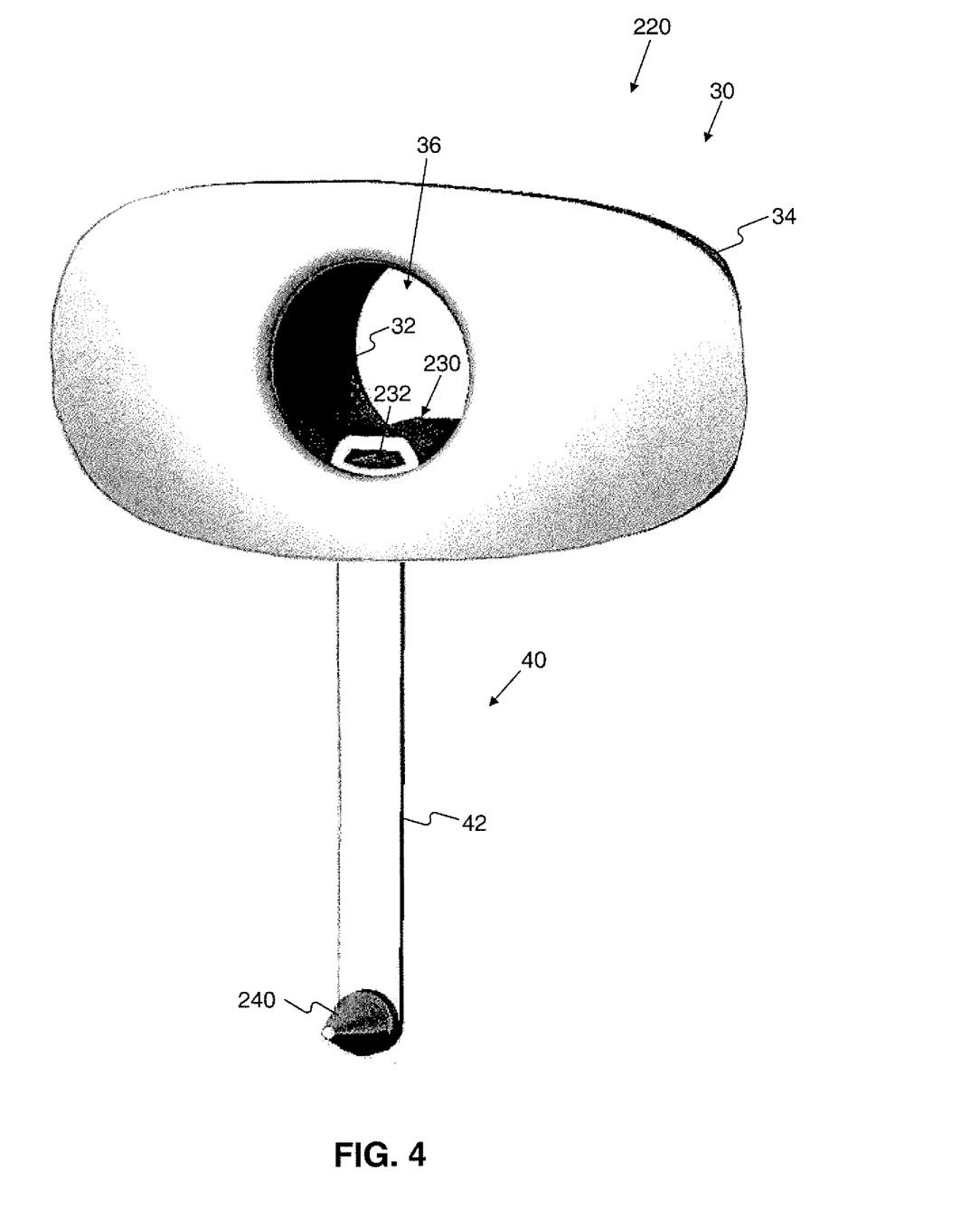
FIG. 4 is a perspective view of a bite guard assembly with a disengaged securing portion, according to yet another exemplary embodiment of the invention.

In the exemplary embodiment shown in FIG. 3, a bite guard assembly 120 may be similar to the bite guard assembly 20 shown in FIGS. 1 and 2 except that the bite guard assembly 120 does not include the securing portion 40 and instead includes a plurality of projections 130 (e.g., six projections) or bumps in passageway 36 of main portion 30. The projections 130 serve as securing portions disposed on a surface of the passageway 36. The projections 130 extend towards an axis or center of the passageway 36 and may extend along the length of the passageway 36 from the front of the bite guard assembly 120 (e.g., the front of the shield 34) to the rear of the bite guard assembly 120 (e.g., the rear of the mouthpiece). The projections 130 may be formed from a material, such as plastic or rubber, that is capable of forming a friction fit with the elongated member of the guide tube that may also allow restricted movement of the elongated member of the guide tube with respect to the bite guard assembly 120. Accordingly, the projections 130 prevent the elongated member from moving freely with respect to the bite guard assembly 120 and the patient's GI tract. These projections may, alternatively, be located on the wedge member 44 or on both components. Furthermore, the projections permit airflow and fluid flow around them while still securing the guide tube.

As described above in connection with the embodiment of the bite guard assembly 20 shown in FIGS. 1 and 2, the operator may select the bite guard assembly 120 from a set of similar bite guard assemblies of various sizes. For example, the size of the bite guard assembly 120 (e.g., dimensions of the mouthpiece 32, the shield 34, and/or the projections 130) may vary according to the patient's characteristics, the size of the elongated member of the guide tube to be inserted into the passageway 36, or other characteristics, as described above. After selecting the appropriate bite guard assembly 120, the selected bite guard assembly 120 may be inserted into the patient's mouth to allow the patient to grip the mouthpiece 32 of the bite guard assembly 120.

The guide tube may be inserted into the passageway 36 in the bite guard assembly 120 and then into the patient's GI tract until the distal end of the guide tube is positioned, e.g., at a floor of the stomach or duodenum. One or more working instruments may be inserted into the lumen in the guide tube. The working instruments may be controlled while the guide tube is advanced into the GI tract.

To hold the guide tube in place with respect to the GI tract and the bite guard assembly 120 (e.g., so that the operator may free both hands to control the working instruments in the guide tube), the operator may release the guide tube. Then, the projections 130, through friction or interference fit, may secure the bite guard assembly 120 in place on the elongated member of the guide tube. The position of the elongated member of the guide tube with respect to the bite guard assembly 120 may remain generally constant until the guide tube is advanced or retracted by the operator. The working instruments may be manipulated through the guide tube to operate on the gall bladder (e.g., during a cholecystectomy) or other body organ. The guide tube may be used as a frame of reference when inserting the working instruments into the body.

To adjust the position of the guide tube with respect to the GI tract and the bite guard assembly 120, the operator may advance or retract the elongated member of the guide tube through the passageway 36 of the bite guard assembly 120. The guide tube may be advanced further into the GI tract by continuing to move through the passageway 36 of the bite guard assembly 120, or the guide tube may be retracted by pulling the guide tube in the opposite direction.

The position of the elongated member with respect to the bite guard assembly 120 is adjustable, thereby allowing customization based on the dimensions of the individual patient's anatomy (e.g., the distance between the mouth and the stomach). Furthermore, the projections 130 prevent the bite guard assembly 120 from moving freely with respect to the elongated member of the guide tube, and therefore, the operator does not have to continuously hold the elongated member. Inadvertent movement of the elongated member, e.g., during surgery, may be prevented. In addition, the bite guard assembly 120 controls the placement of the patient's tongue and prevents the patient from biting the elongated member of the guide tube, thereby protecting the guide tube and working instruments inserted into the guide tube.

The operator may control the working instruments with one hand while advancing the guide tube into the patient's GI tract with the other hand. For example, after the operator inserts the guide tube into the bite guard assembly 120 and as the guide tube advances through the GI tract, the operator's left hand may coordinate the movement of the working instruments while the operator's right hand may control the positioning of the guide tube in the GI tract. To permit the operator to use both hands to control the working instruments (e.g., to perform certain tasks, such as passing the working instruments through the lumen of the guide tube, manipulating the working instruments, etc.), the operator may let go of the guide tube with the right hand, and the projections 130 may hold the guide tube in place with respect to the bite guard assembly 120. Then, the operator is free to use both hands to control the working instruments.

In the exemplary embodiment shown in FIG. 4, a bite guard assembly 220 may be similar to the bite guard assembly 20 shown in FIGS. 1 and 2 except that the bite guard assembly 220 includes a projection instead of the wedge member 44 in the securing portion 40 and includes an expandable member 230 disposed on the surface of passageway 36 of main portion 30. In the embodiment shown in FIG. 4, the projection of the securing portion 40 includes a conical projection 240. Like the bite guard assembly 20 shown in FIGS. 1 and 2, the connecting member 42 may be omitted such that the conical projection 240 is not connected to the main portion 30 of the bite guard assembly 220.

The expandable member 230 may extend along the length of the passageway 36 from the front of the bite guard assembly 220 (e.g., the front of the shield 34) to the rear of the bite guard assembly 220 (e.g., the rear of the mouthpiece), and may include a channel 232. The channel 232 may extend along passageway 36. The conical projection 240 may be inserted into the channel 232 to cause the expandable member 230 to expand towards the axis or center of the passageway 36. Thus, the expandable member 230 is changeable between an expanded configuration when the conical projection 240 is inserted into the channel 232 in the expandable member 230 and a collapsed configuration when the projection 240 is not inserted into the channel 232. In the collapsed configuration, at least a portion of the expandable member 230 may be collapsed against the surface of the passageway 36 when the elongated member of the guide tube is inserted into the passageway 36. The expandable member 230 may be formed from a flexible material, such as a plastic, rubber, or fabric material, which may expand when the conical projection 240 is inserted into the channel 232. Although the projection is illustrated and described as a conical projection 240. In general, the projection may be of any shape. For instance, the projection may be cylindrically shaped, tapered, or may be a blunt end tool.

When the elongated member of the guide tube is inserted into the passageway 36 and the conical projection 240 is engaged by being inserted into the channel 232, the expanded channel 232 may form a friction or interference fit with the elongated member of the guide tube, thereby securing the bite guard assembly 220 to the guide tube. After the conical projection 240 is inserted into the channel 232, the conical projection 240 may be disengaged by being removed from the channel 232 to allow an adjustment of the location of the bite guard assembly 220 on the guide tube and positioning of the guide tube in the body. FIG. 4 shows the conical projection 240 removed from the channel 232 such that the conical projection 240 is disengaged, thereby allowing adjustment of the location of the bite guard assembly 220 on the guide tube.

The conical projection 240 may be configured to be inserted into the channel 232 of the expandable member 230 when the elongated member of the guide tube is disposed in the passageway 36. As a result, the conical projection 240 may secure the bite guard assembly 220 onto the guide tube through friction or interference. Insertion of the conical projection 240 helps to prevent inadvertent movement of the elongated member with respect to the bite guard assembly 220 while still allowing a portion of the passageway 36 to be unobstructed to allow air to flow freely into and out of the patient's mouth. Optionally, the conical projection 240 may include a tab (not shown) or other feature for allowing the operator to remove the conical projection 240 from the channel 232. Alternatively, the conical projection 240 may have another shape besides conical, e.g., cylindrical, rectangular prism, etc.

As described above in connection with the embodiment of the bite guard assembly 20 shown in FIGS. 1 and 2, the operator may select the bite guard assembly 220 from a set of similar bite guard assemblies of various sizes. For example, the size of the bite guard assembly 220 (e.g., dimensions of the mouthpiece 32, the shield 34, and/or the conical projection 240) may vary according to the patient's characteristics, the size of the elongated member of the guide tube to be inserted into the passageway 36, or other characteristics.

Furthermore, since the projection 240 is conical, the depth to which the conical projection 240 is inserted into the channel 232 in the expandable member 230 may vary. Therefore, each bite guard assembly 220 may accommodate different guide tubes of various sizes. For example, if the passageway 36 and the guide tube are similar in diameter, the bite guard assembly 220 may be secured to the guide tube by inserting only a tip portion (e.g., the portion of smaller diameter) of the conical projection 240 into the channel 232. However, if the passageway 36 is much larger than the guide tube, the bite guard assembly 220 may be secured to the guide tube by inserting the entire conical projection 240 or a substantial portion thereof into the channel 232. Accordingly, different guide tubes of various sizes may be accommodated in the bite guard assembly 220 as long as the diameter of the guide tube does not exceed a predetermined maximum size (e.g., the diameter of the passageway 36) or is less than a predetermined minimum size (e.g., the difference between the diameter of the passageway 36 and the maximum diameter of the conical projection 240). As a result, according to one embodiment, the operator may select the appropriate bite guard assembly 220 based on the patient's characteristics and based on whether the size of the guide tube is within a predetermined range of sizes appropriate for the particular bite guard assembly 220. Then, the selected bite guard assembly 220 may be inserted into the patient's mouth to allow the patient to grip the bite guard assembly 220.

The guide tube may be inserted into the passageway 36 in the bite guard assembly 220 and then into the patient's GI tract until the distal end of the guide tube is positioned, e.g., at a floor of the stomach or duodenum. One or more working instruments may be inserted into the lumen in the guide tube. The working instruments may be controlled while the guide tube is advanced into the GI tract.

To hold the guide tube in place with respect to the GI tract and the bite guard assembly 220 (e.g., so that the operator may free both hands to control the working instruments in the guide tube), the operator may engage the conical projection 240 by inserting it into the channel 232 in the expandable member 230. The position of the elongated member of the guide tube with respect to the bite guard assembly 220 may remain generally constant until the conical projection 240 is removed from the channel 232. In some embodiments, the working instruments may be manipulated through the guide tube to operate on the gall bladder (e.g., during a cholecystectomy) or other body organ. The guide tube may be used as a frame of reference when inserting the working instruments into the body.

To adjust the position of the guide tube with respect to the GI tract or other body lumen and the bite guard assembly 220, the operator may release the bite guard assembly 220 from the elongated member of the guide tube by removing or disengaging the conical projection 240 from the channel 232. The guide tube may be advanced further into the GI tract or other body lumen by continuing to move through the passageway 36 of the bite guard assembly 220, or the guide tube may be retracted by pulling the guide tube in the opposite direction.

The position of the elongated member with respect to the bite guard assembly 220 is adjustable, thereby allowing customization based on the dimensions of the individual patient's anatomy (e.g., the distance between the mouth and the stomach). Furthermore, the conical projection 240 secures the bite guard assembly 220 onto the elongated member when the conical projection 240 is inserted into the channel 232 such that the elongated member may be prevented from moving with respect to the patient's GI tract or other body lumen. Therefore, the operator does not have to continuously hold the elongated member. Inadvertent movement of the elongated member, e.g., during surgery, may be prevented. In addition, the bite guard assembly 220 controls the placement of the patient's tongue and prevents the patient from biting the elongated member of the guide tube, thereby protecting the guide tube and working instruments inserted into the guide tube.

The operator may control the working instruments with one hand while advancing the guide tube into the patient's GI tract with the other hand. For example, after the operator inserts the guide tube into the bite guard assembly 220 and as the guide tube advances through the GI tract, the operator's left hand may coordinate the movement of the working instruments while the operator's right hand may control the positioning of the guide tube in the GI tract. To permit the operator to use both hands to control the working instruments (e.g., to perform certain tasks, such as passing the working instruments through the lumen of the guide tube, manipulating the working instruments, etc.), while holding the elongated member of the guide tube with the right hand, the operator may use the left hand to release the working instruments and insert the conical projection 240 into the channel 232 of the expandable member 230 to hold the guide tube in place. Then, the operator is free to use both hands to control the working instruments.

In various embodiments, the guide tube set forth herein may be used with any of the bite guard assemblies 20, 120, 220 in any combination. Any aspect set forth in any embodiment may be used with any other embodiment set forth herein. Every device and apparatus set forth herein may be used in any suitable medical procedure, and may be advanced through any suitable body lumen and body cavity. For example, the apparatuses and methods described herein may be used in any natural body lumen or tract, including those accessed orally, vaginally, or rectally.

It will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only. The following disclosure identifies some other exemplary embodiments.

What is claimed is:

1. A medical device, comprising:
a bite guard assembly configured to restrict sliding movement of an elongated member relative to the bite guard assembly, the bite guard assembly including:
a main portion including a mouthpiece, the main portion including a surface defining a passageway for receipt of the elongated member therethrough;
an expandable member on the surface, the expandable member including a channel; and
a securing portion including a projection configured to be inserted into the channel in the expandable member, the securing portion configured to restrict movement of the elongated member through the passageway and configured to be disposed between the surface and the elongated member.

2. The medical device of claim 1, wherein the securing portion is configured to form a friction or interference fit with the elongated member.

3. The medical device of claim 2, wherein the projection is configured to form the friction or interference fit with the elongated member.

4. The medical device of claim 1, wherein the bite guard assembly is configured to include a gap between the elongated member and the surface to allow air to pass therethrough.

5. The medical device of claim 1, wherein the expandable member is configured to transform from a collapsed configuration to an expanded configuration when the projection is inserted into the channel.

6. The medical device of claim 5, wherein the expandable configuration is a configuration where the expandable member interfaces with the elongated member to restrict movement of the elongated member relative to the bite guard assembly.

7. The medical device of claim 1, wherein the projection is conical, cylindrically shaped, tapered, or blunt.

8. The medical device of claim 1, wherein the elongated member is a flexible guide tube.

9. The medical device of claim 1, wherein the securing portion further includes a connecting member connecting the projection to the main portion of the bite guard assembly.

10. The medical device of claim 1, wherein the expandable member is configured to form a friction or interference fit with the elongated member when the projection is inserted into the channel in the expandable member.

11. The medical device of claim 1, wherein the main portion and the securing portion are configured to restrict movement of elongated members of varying diameters.

12. The medical device of claim 1, wherein the expandable member is flexible.

13. The medical device of claim 1, wherein the main portion further includes a shield integral with the mouthpiece.

14. A medical device, comprising:
a bite guard assembly configured to restrict sliding movement of an elongated member relative to the bite guard assembly, the bite guard assembly including:
a main portion including a mouthpiece, the main portion including a surface defining a passageway for receipt of the elongated member therethrough; and
a securing portion including a wedge member configured to be inserted between the elongated member and the surface of the bite guard assembly,
wherein the elongated member includes one or more protrusions configured to interface with the wedge member and restrict movement of the elongated member through the passageway.

15. The medical device of claim 14, wherein the bite guard assembly is configured to include a gap between the elongated member and the surface to allow air to pass therethrough.

16. A bite guard assembly comprising:
a mouthpiece;
a front shield formed integrally with the mouthpiece, wherein an inner surface of the mouthpiece and the front shield defines a passageway to allow an elongated member to pass therethrough; and
a securing portion configured to be disposed between the inner surface and the elongated member;
wherein the inner surface includes an expandable member having a channel, and the securing portion includes a projection configured to be inserted into the channel of the expandable member.

17. The bite guard assembly of claim 16, wherein the expandable member is configured to transform from a collapsed configuration to an expanded configuration when the projection is inserted into the channel.

18. The bite guard assembly of claim 16, wherein the expandable member is flexible.

19. The bite guard assembly of claim 16, wherein the projection is configured to form a friction or interference fit with the elongated member.

20. The bite guard assembly of claim 16, wherein the projection is conical, cylindrically shaped, tapered, or blunt.

* * * * *